(12) United States Patent
Le Ricque

(10) Patent No.: US 10,933,391 B2
(45) Date of Patent: Mar. 2, 2021

(54) PRESSURISED APPLIANCE WITH A COVER COMPRISING A SAMPLING TIP HAVING AT LEAST ONE CLOSABLE OPENING

(71) Applicant: BIOMÉRIEUX, Marcy l'Etoile (FR)

(72) Inventor: Guilhem Le Ricque, Rennes (FR)

(73) Assignee: BIOMERIEUX, Marcy l'Etoile (FR)

( * ) Notice: Subject to any disclaimer, the term of this patent is extended or adjusted under 35 U.S.C. 154(b) by 248 days.

(21) Appl. No.: 15/757,581

(22) PCT Filed: Aug. 31, 2016

(86) PCT No.: PCT/FR2016/052159
§ 371 (c)(1),
(2) Date: Mar. 5, 2018

(87) PCT Pub. No.: WO2017/051090
PCT Pub. Date: Mar. 30, 2017

(65) Prior Publication Data
US 2018/0243708 A1 Aug. 30, 2018

(30) Foreign Application Priority Data

Sep. 3, 2015 (FR) ...................................... 1558154

(51) Int. Cl.
| | |
|---|---|
| *A61L 2/08* | (2006.01) |
| *B01D 11/04* | (2006.01) |
| *A61L 2/00* | (2006.01) |
| *B01J 3/04* | (2006.01) |
| *C12M 1/00* | (2006.01) |
| *C12M 1/12* | (2006.01) |
| *C12M 1/34* | (2006.01) |
| *C12M 1/26* | (2006.01) |

(52) U.S. Cl.
CPC ................ *B01J 3/04* (2013.01); *C12M 23/38* (2013.01); *C12M 33/00* (2013.01); *C12M 37/00* (2013.01); *C12M 41/40* (2013.01); *C12M 99/00* (2013.01)

(58) Field of Classification Search
CPC ........ A61K 31/00; A61K 38/00; A61K 39/00; A61L 2/07; A61L 2202/20; B01J 3/04
USPC ......... 422/26, 256, 260–261, 283, 285, 292, 422/295, 307; 134/104.3, 105
See application file for complete search history.

(56) References Cited

U.S. PATENT DOCUMENTS

2014/0377417 A1   12/2014   Martinez

OTHER PUBLICATIONS

Morscher, Elmar et al., "Mediaclave Mode d'emploi.", V10_01_MEDIACLAVE_FR.pdf, (2013).*

(Continued)

*Primary Examiner* — Monzer R Chorbaji
(74) *Attorney, Agent, or Firm* — Oliff PLC

(57) ABSTRACT

A pressurized appliance comprising, a tank, suitable for receiving liquid contents, a cover, suitable for sealing the tank in a closed position, said cover comprising a sampling tip, said tip comprising a cannula capable of being in contact with the contents when the cover is in the closed position, the sampling tip comprising at least one sealable orifice making it possible, when the cover is in its closed position and said orifice is a through-orifice, to ensure a pressure equilibrium between the inside of the cannula and the inside of the tank, and when the cover is in its closed position and said orifice is sealed, to sample the contents via the cannula.

15 Claims, 7 Drawing Sheets

(56) References Cited

OTHER PUBLICATIONS

English Translation of Morscher, Elmar et al., "Mediaclave Mode d'emploi.", V10_01_MEDIACLAVE_FR.pdf, (2013).*

Morscher, Elmar et al., "Mediaclave Mode d'emploi.", http://www.integra-biosciences.com/sites/pdf/operating_instructions/136950_V10_01_MEDIACLAVE_FR.pdf, (2013).

Biomerieux. "Media Preparation Masterclave 09 Media Projector.", http://www.dwscientific.co.uk/assets/product-pdfs/Masterclave%20Media%20Preparators/Masterclave%2009/010_3%20Masterclave%2009.pdf, (2012).

Nov. 18, 2016 Written Opinion of the International Search Authority issued in Patent Application No. PCT/FR2016/052159.

Nov. 18, 2016 International Search Report issued in Patent Application No. PCT/FR2016/052159.

\* cited by examiner

PRESSURISED APPLIANCE WITH A COVER COMPRISING A SAMPLING TIP HAVING AT LEAST ONE CLOSABLE OPENING

The present invention relates to the field of pressurized appliances, in particular to the appliances for preparing culture media or diluents, more particularly powdered culture media. These appliances, also referred to as automated culture media preparators, are instruments used in particular by laboratories for the production of culture media from dehydrated media. The invention relates more particularly to a pressurized appliance comprising a sampling tip that makes it possible to prevent the contents of the appliance from overflowing.

The operating principle of automated culture media preparators is the following: the operator mixes dehydrated culture medium with water in a bucket immersed in a tank that may be closed by a cover. Water is added to the tank in order to carry out water-bath heating of the contents of the bucket. A magnetic stirrer is placed at the bottom of the bucket. Once the cover of the tank is hermetically closed, the appliance begins by mixing the water and the dehydrated culture medium then will sterilize the product by heating it for a defined period. The contents of the tank then reaches a pressure approximately between 1 bar and 1.5 bar. After cooling, the medium is then sampled directly in the bucket of the automated preparator then poured hot into petri dishes in the case of an agar medium or kept in liquid form in the case of a broth.

The quality and the fertility of the culture media prepared, whether they are in the form of agar or broth, therefore depends directly on the ability of the automated preparator to accurately control the temperature and the pressure during the preparation. Moreover, since the temperature of the medium being prepared generally reaches 121° C., and this being under pressure during this operation, it is essential for an automated preparator to guarantee the safety of the operator and his/her working environment by preventing any spillage of the contents of the bucket before, during or following its preparation. Moreover, it is essential for an automated preparator to guarantee the sterility of the prepared medium up to the sampling step.

The automated preparators currently sold by the applicant, such as the Masterclave M09 (bioMérieux, ref: AESAP1080) have a cover comprising a sampling nozzle that makes it possible to sample the contents of the bucket. For this, the nozzle is connected to a cannula that extends inside the tank until it reaches the bottom of the bucket. During the culture medium preparation step, the sampling nozzle is sealed by a cap. Once the medium or the diluent is prepared, the operator removes the cap and connects the sampling nozzle to a peristaltic pump so as to suck up the contents of the bucket through the cannula.

However, when closing the cover of the automated preparator, the pressure exerted by the movement of the cover on the contents of the bucket may lead to a rapid rise of the contents through the cannula. If the operator has not correctly tightened or has neglected to add the cap of the sampling nozzle or other caps present on the cover, the contents of the bucket then spills out of the tank which is obviously not desirable. Moreover, during the rise in temperature and in pressure of the appliance, the vapor contained in the tank will exert pressure on the liquid contents of the bucket. If the cap of the sampling nozzle is poorly tightened or absent, the contents of the bucket will then seek to escape by rising back up through the cannula and will spill out of the tank, it being possible for the contents to have already reached a temperature that is dangerous for the operator. Moreover, a leak of vapor through the nozzle cap may also occur during the rise in temperature and in pressure of the appliance if the latter is poorly tightened.

This spillage is all the more undesirable since it leads to the partial or even complete loss of the prepared medium, the sterility of the latter no longer being guaranteed. Furthermore, the operation for cleaning the appliance when it is covered with agar medium is particularly tedious.

This spillage may also occur during pressurization tests of the tank with the aid of a compressor. This type of test may in particular be carried out at the start of the cycle to verify the leaktightness of the cap(s) of the cover sealing the tank.

There is therefore an unmet need to provide a pressurized appliance that makes it possible to guarantee the safety of the operators and of the property surrounding the pressurized appliance while enabling the simple and rapid sampling of the whole of the contents of the pressurized appliance following its preparation.

Another objective of the invention is to provide a pressurized appliance that is simple and quick to maintain.

In order to achieve these objectives, a pressurized appliance has been developed comprising:
- a tank, suitable for receiving liquid contents,
- a cover, suitable for sealing the tank in a closed position, said cover comprising a sampling tip, said tip comprising a cannula capable of being in contact with the contents when the cover is in the closed position,
- the sampling tip comprises at least one sealable orifice making it possible, when the cover is in its closed position and said orifice is a through-orifice to ensure a pressure equilibrium between the inside of the cannula and the inside of the tank, and when the cover is in its closed position and said orifice is sealed, to sample the contents via the cannula.

Advantageously, the sampling tip comprises several sealable orifices, distributed radially over the part of the tip extending into the tank, preferentially close to the cover.

Advantageously, the sampling tip comprises an intermediate part that is removable relative to the cover, preferentially by screwing.

Advantageously, said intermediate part is suitable for cooperating with a tightening means, said part extending preferably into the tank when the cover is in the closed position.

Advantageously, the pressurized appliance comprises a removable sampler, said removable sampler sealing the sealable orifice when the latter is positioned and held in the sampling tip.

Advantageously, the removable sampler is suitable for cooperating with a suction means such as a peristaltic pump.

Advantageously, the pressurized appliance comprises a cap, the orifice(s) being through-orifice(s) and the sampling tip being sealed when the cap is positioned and held on the sampling tip.

Advantageously, the cannula comprises a beveled end.

Advantageously, the cannula comprises two connectable parts, at least one of the connectable parts preferably being flexible.

Advantageously, the tank has a curved bottom.

Advantageously, the tank is suitable for receiving a bucket in order to contain the liquid contents, the cannula extending into the bucket when the cover is in the closed position.

The invention also relates to the use of a pressurized appliance as described above for the preparation of a culture medium.

A bucket is understood to mean a part comprising a cylindrical or frustoconical wall and a bottom, suitable for containing constituents such as liquids, powders or a gel, in particular for the preparation of a culture medium to be sterilized. Within the meaning of the present invention, a bucket is generally made of stainless steel, by drawing. The bottom of the bucket may have a curve oriented toward the inside of the bucket so as to distribute liquid contents in an annular zone located in the vicinity of the contact between the bottom of the bucket and the wall of the bucket. This curve has the advantage of facilitating the sampling of the liquid by minimizing the surface area over Which the latter is distributed as the level of liquid to be sampled decreases.

A tank is understood to mean a cavity made in the housing of a pressurized appliance, capable of receiving a bucket. A tank may be composed of three parts, generally welded together, a plate, a wall and a bottom. The plate is a flat part from which a generally circular part, corresponding to the open part of the tank, is cut out. The tank also comprises a cylindrical or frustoconical wall, in connection with the open part and the bottom. The wall may be produced by a shell ring that is cut then roiled and welded to the plate. The bottom is generally drawn then welded to the wall. The plate of the tank corresponds to the upper part of the housing so that the closure of the cover results in the sealing of the tank.

A cover is understood to mean an assembly that is mobile relative to the housing, capable of sealing the tank in a closed position. In order to guarantee the safety of the personnel in the vicinity of the appliance and the pressure resistance, the cover also has a locking position that guarantees a hermetic closure of the tank and a pressure resistance up to a certain threshold, generally defined according to the regulations in force in the country in which the appliance is used.

The invention will be clearly understood and other features and advantages of the invention will become clearly apparent from the description which is given below, by way of nonlimiting indication, with reference to the drawing, in which.

For simplification, the parts or elements of one embodiment that are found in an identical or similar manner in another embodiment will be identified by the same numerical references and will not be described again.

Figure 1:
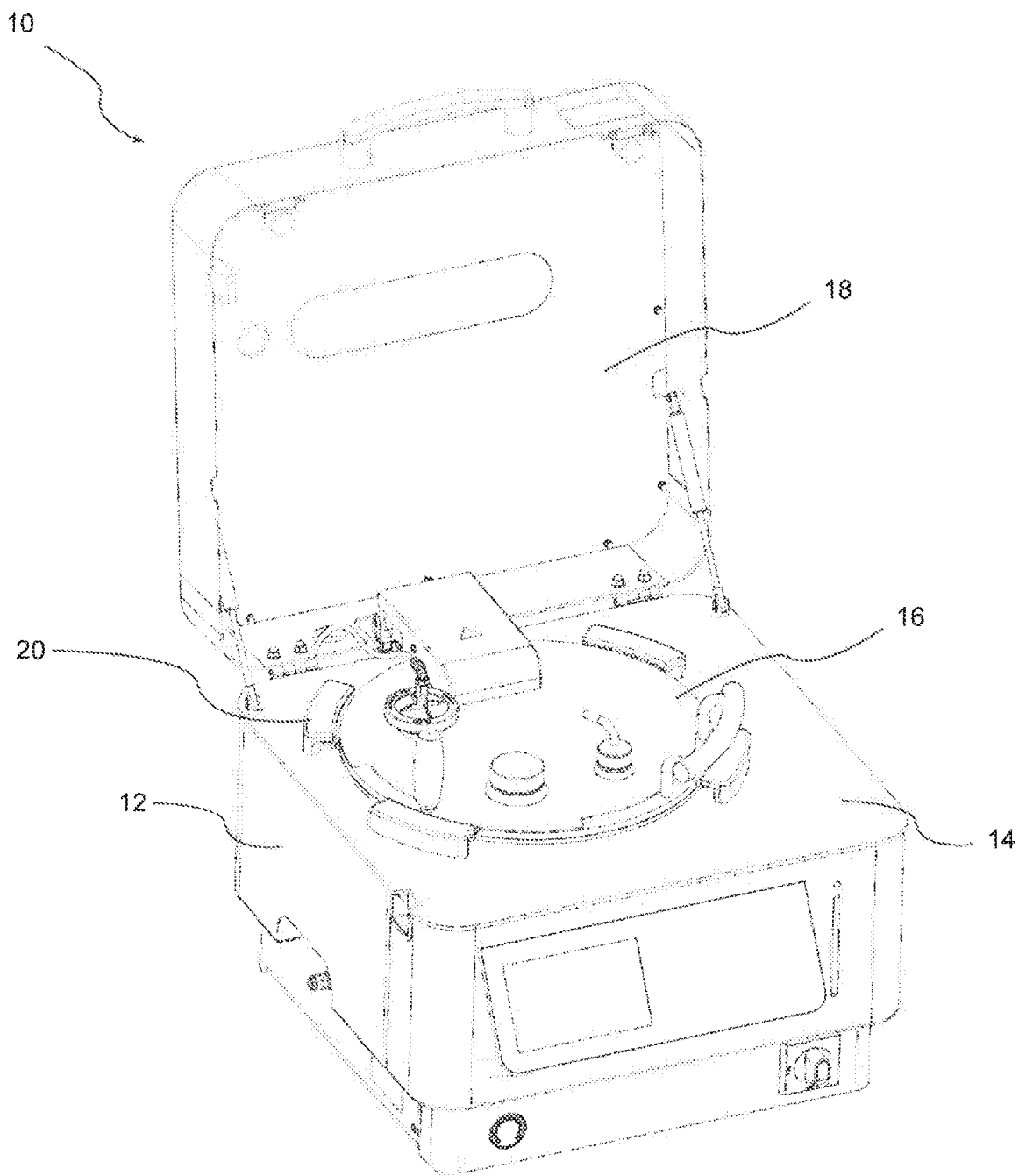
FIG. 1 is a representation, in perspective, of a pressurized appliance according to the invention.

According to one embodiment of the invention, FIG. 1 represents a pressurized appliance also referred to as an automated preparator 10 comprising a housing 12 having an upper part or plate 14 into which a tank is fitted. The tank is presented sealed by a cover 16 that can be protected by a removable casing 18. The tank is suitable for receiving a bucket. The cover 16 may be held in a locking position by four L-shaped claws 20 that jut out over the plate 14.

Figure 2:
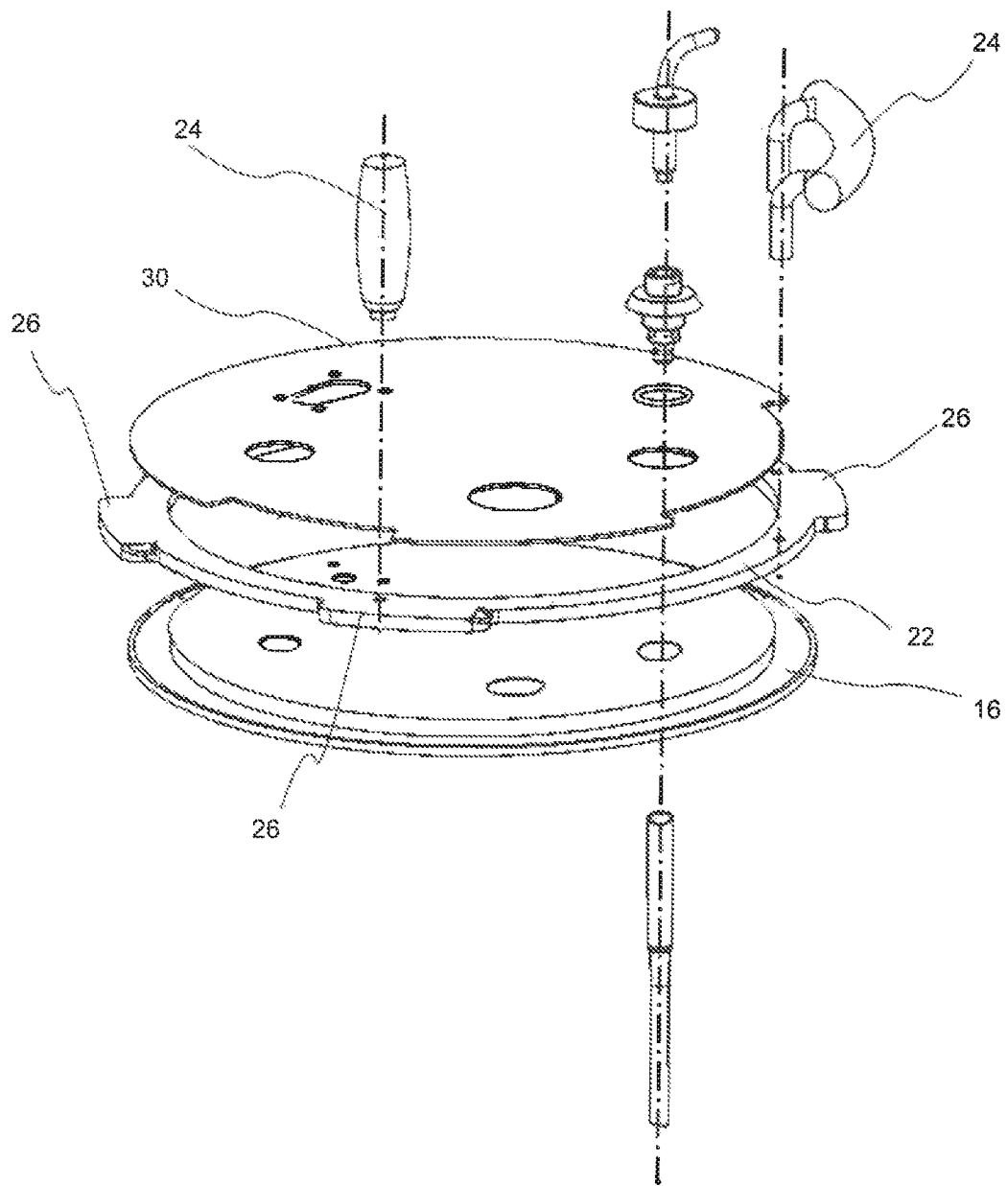
FIG. 2 is a representation, as an exploded view, of the cover of the pressurized appliance.

For this, and as represented in FIG. 2, the cover 16 comprises a ring 22, attached and rotatably mobile relative to the cover and able to be moved from a free position to a locking position by means of two handles 24, said ring comprising four locking lugs 26 that extend radially and cooperate with the claws 20 when the cover is in the closed position and when said ring is in the locking position so as to be able to pressurize the tank. The cover also has a lip seal 28, visible in FIGS. 5 to 7 and a cowl 30. The seal is attached to the cover so as to ensure the leaktightness of the tank when the cover is in the closed position and the ring is in the locking position.

Figure 3:
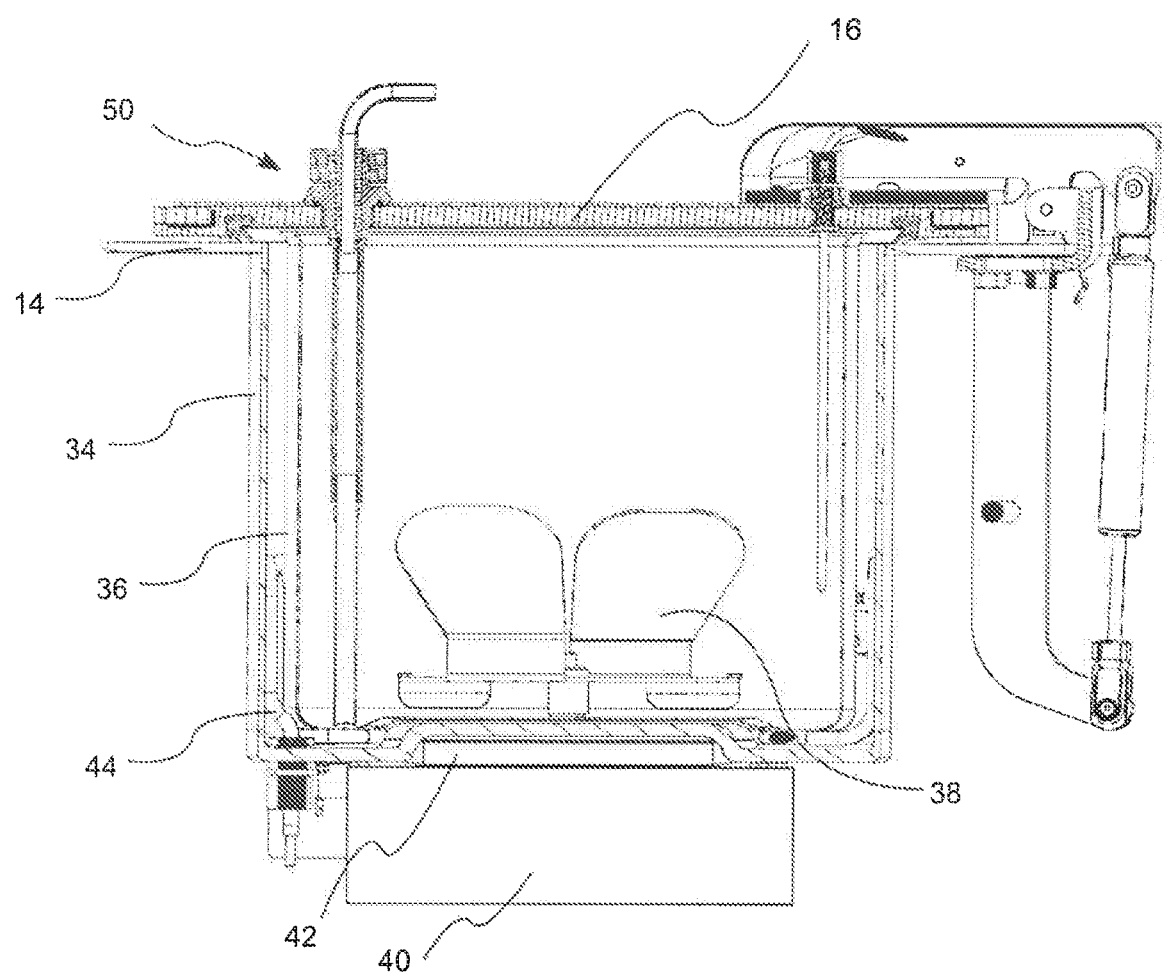
FIG. 3 is a representation, in cross section, of the pressurized appliance.

As represented in FIG. 3, the tank 34 is fitted in the plate 14 and contains a bucket 36. A magnetic stirrer 38 is placed in the bottom of the bucket. The magnetic stirrer is a part made of ferromagnetic material, for instance made of stainless steel, making it possible to homogenize the temperature of the contents of the bucket by carrying out cyclical rotations. The magnetic stirrer makes it possible for example to homogenize a culture medium being prepared and to prevent the appearance of waste due for example to a local overheating of the medium. A motor 40 is attached under the tank and rotates a plate 42 where magnets are present, thus driving the stirrer placed in the bucket, in contact with the contents. Three heating resistors 44 are positioned in the tank around the bucket and make it possible to regulate the temperature of the tank and of the contents of the bucket.

A sampling tip 50 is screwed into the cover 16.

Figure 4:
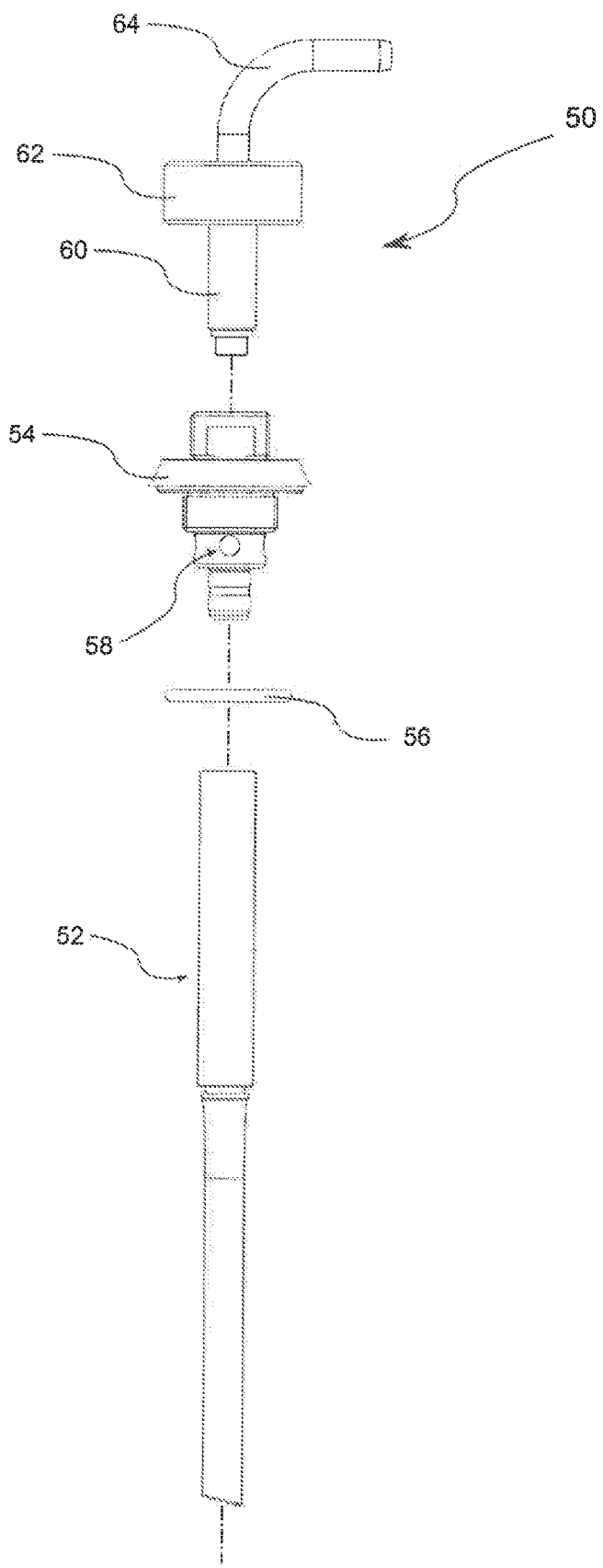
FIG. 4 is a representation, as an exploded view, of the sampling tip of the pressurized appliance.
Figure 5:
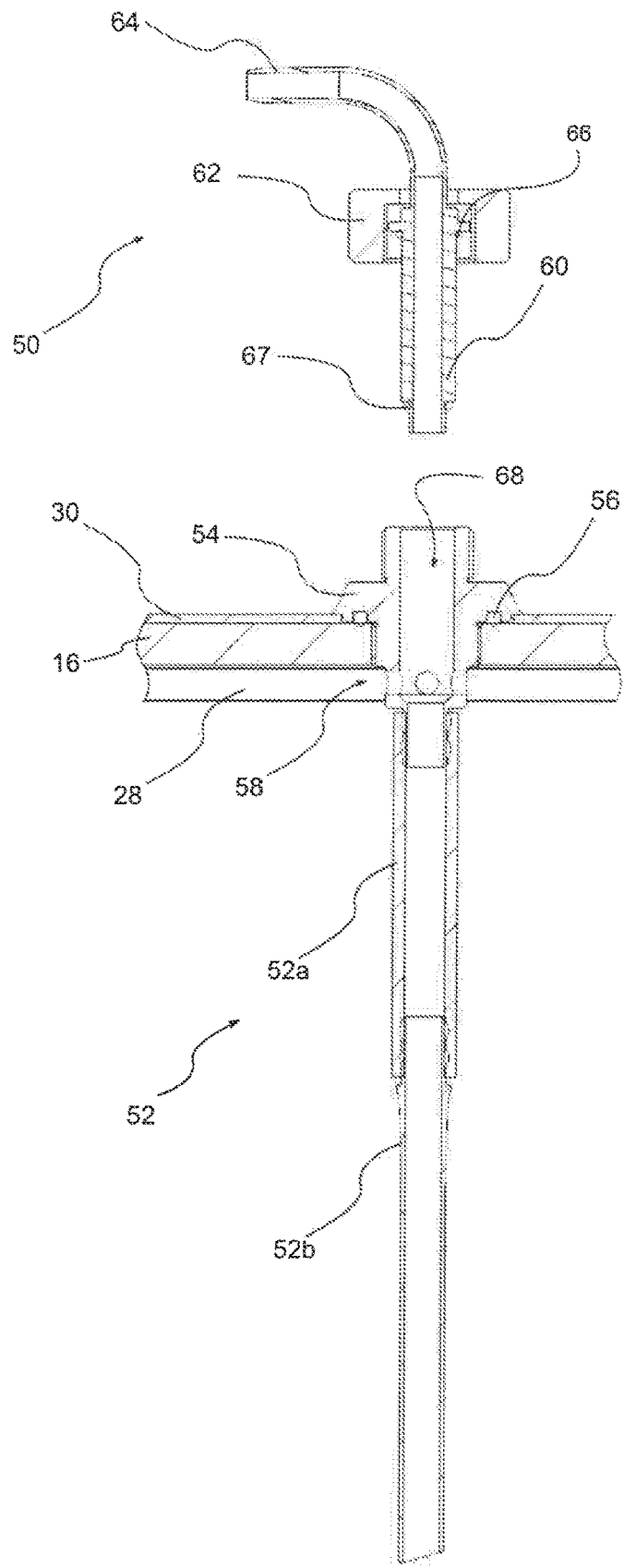
FIG. 5 is a representation, in cross section, of the cover, the sealable orifices of the sampling tip being through-orifices.

As represented in FIGS. 4 and 5, the sampling tip 50 comprises a cannula 52, intended to extend into the tank, more specifically into the bucket, so as to be able to sample the contents of the bucket by suction through the cannula. The cannula 52 is advantageously made of two connectable parts 52a, 52b, which are preferentially interlocked. The part 52b has a beveled end that cooperates with the curved bottom of the bucket in order to be able to sample a maximum amount of the contents. The part 52a is advantageously made of a flexible material such as silicone in order to facilitate the opening and closure of the cover of the tank. The part 52b is advantageously made of stainless steel or any other material that makes it possible to sufficiently weight the cannula 52 so that the end thereof is as close as possible to the bottom of the tank or of the bucket when the cover of the tank is closed. The cannula 52 is itself interlocked in an intermediate part 54 intended to be screwed onto the cover 16 of the appliance. The leaktightness of the screwing is ensured by an O-ring 56. The intermediate part 54 is open, thus making it possible to create a sampling channel 68 between the outside of the appliance and the cannula when this cannula is interlocked. The sampling channel 68 extends along a longitudinal axis similar to that of the cannula. The intermediate part 54 also comprises four sealable orifices 58 that connect the tank, the inside of the cannula and the sampling channel 68 when these are open. The four sealable orifices 58 are distributed radially around the axis of the sampling channel 68.

The sampling tip 50 may be coupled to a removable sampler 60 that can be inserted into the sampling channel 68 and screwed onto the intermediate part 54 via a ring 62. The sampling tip 50 may also be sealed by a cap 70, represented in FIG. 7, screwed onto the intermediate part 54 and thus sealing the sampling channel 68 while leaving the sealable orifices 58 open in order to allow the circulation of air between the inside of the cannula 52 and the tank.

In order to carry out a culture medium or diluent preparation step, the sampling channel 68 is sealed by a cap 70 screwed onto the intermediate part 54. In the case where another opening 80 is present on the cover, this opening is also sealed using a cap 82, here a screw cap, visible in FIG. 7. During this step, the air circulates freely between the inside of the cannula and the sealable orifices 58, thus preventing the creation of a pressure differential between these two cavities that may lead to liquid rising up in the cannula. In order to pressurize the tank, the cover comprises a nozzle for an intake of air originating from a compressor. This inlet has a filter so that the air that passes therethrough also remains sterile. During the heating of the tank, before the temperature of the medium reaches 100° C., vapor is formed in the tank but this vapor does not pass through this filter owing to a non-return valve. The vapor thus formed remains contained in the tank and circulates freely in the cannula, also exerting pressure on the liquid contents of the cannula. The liquid level in the cannula is then similar to that of the bucket.

Figure 6:
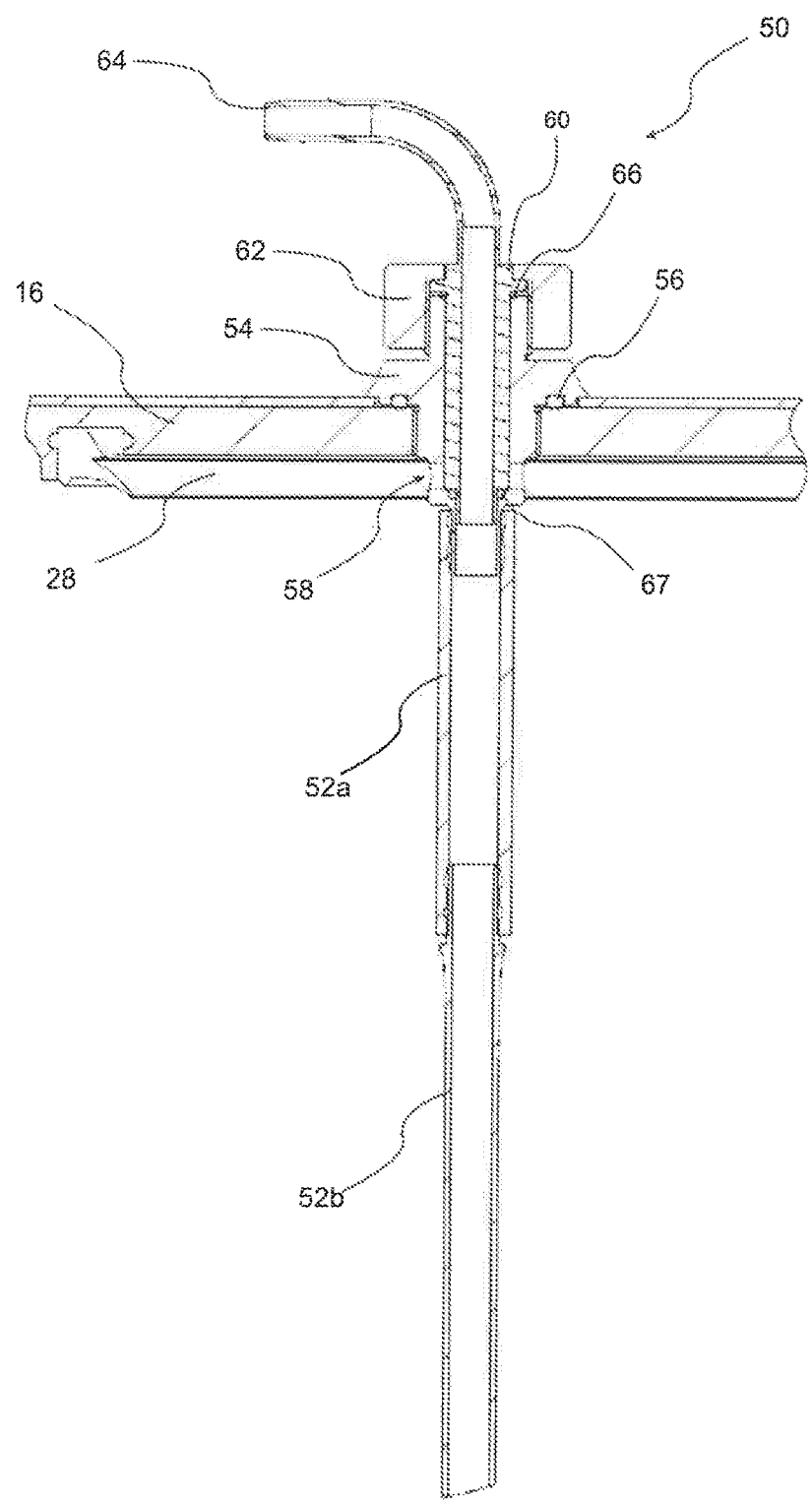
FIG. 6 is a representation, in cross section, of the cover, the sealable orifices of the sampling tip being sealed.
Figure 7:
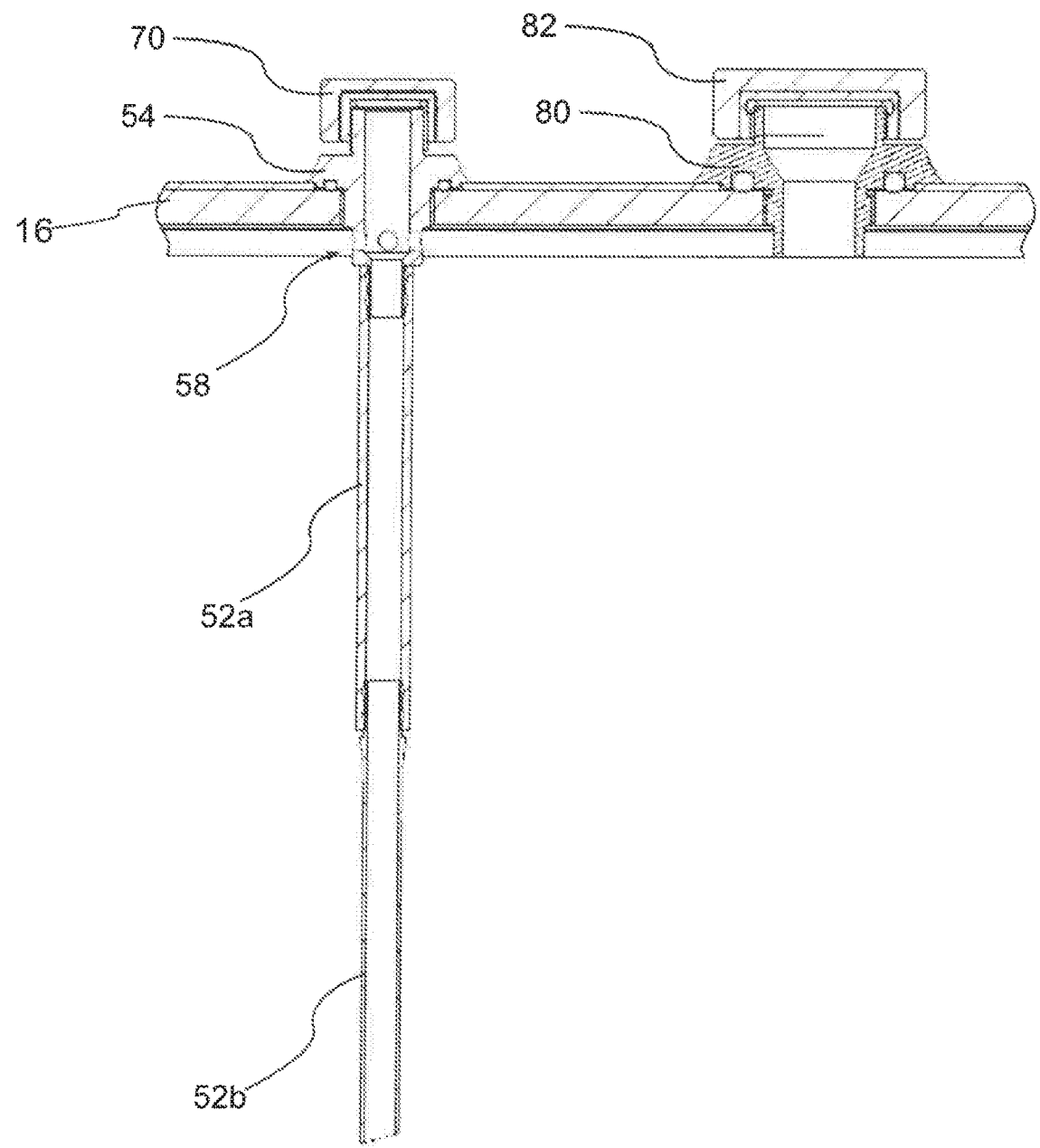
FIG. 7 is a representation, in cross section, of the cover, the sampling tip being sealed by a cap and the sealable orifices being through-orifices.

The culture medium or diluent preparation step ends with the cooling of the tank. The volume occupied by the vapor in the tank then decreases, creating a vacuum. Air is then sucked through the above filter in order to rebalance the pressure of the tank with the atmospheric pressure. Once equilibrium has been established, the operator then screws the sampler 60 onto the intermediate part 54 in place of the cap, as represented in FIG. 6. The removable sampler 60 is stored beforehand in a sterile bag and autoclaved between each preparation cycle. The leaktightness of the screwing of the sampler once screwed on is ensured by two O-rings 66 and 67. This configuration makes it possible to provide a simple and compact removable sampler 60 that can be easily handled and sterilized between each operation, especially owing to the fact that the cannula remains attached to the cover and does not have to be handled during the sampling of the prepared medium.

The removable sampler 60 has a cylindrical part extending along a longitudinal axis, the outer diameter of which is adjusted closely with the inner diameter of the sampling channel 68 of the intermediate part 54. This adjustment and also the O-ring 67 placed between the end of the removable sampler 60 and the intermediate part 54 make it possible to seal the sealable orifices 58 when this sampler is inserted and screwed onto the intermediate part. This therefore prevents the air from circulating from the inside, the non-immersed part, of the tank to the inside of the cannula and to the outside, while the tank contains a liquid to be sampled. The removable sampler 60 has one end 64 that can be connected to a sampling means such as a peristaltic pump or a culture media dispenser such as APS ONE, sold by the applicant. The operator then connects a sampling means to the end 64 in order to pump the prepared medium.

Alternatively, the sampler comprises a cylindrical part comprising four orifices that cooperate with the sealable orifices of the intermediate part. In a first position of the sampler, the orifices are positioned in line with the sealable orifices so as to ensure pressure equilibrium between the tank and the inside of the cannula. The sampler may then be closed by a cap, so as to be able to pressurize the tank.

In a second position of the sampler, the cylindrical part is moved by rotation or translation so as to seal the sealable orifices. The sampler may then be connected to a sampling means, so as to pump the contents of the tank.

The invention claimed is:

1. A pressurized appliance comprising:
   a tank configured to receive liquid contents;
   a cover configured to seal the tank in a closed position;
   a sampling tip removably attached to the cover, the sampling tip comprising:
      a cannula configured to contact the liquid contents when the cover is in the closed position, and
      at least one sealable orifice configured to ensure a pressure equilibrium between the inside of the cannula and the inside of the tank when the cover is in the closed position and the pressurized appliance is in a first mode, and configured to allow sampling of the contents via the cannula when the cover is in the closed position and the pressurized appliance is in a second mode; and
   a sampler removably attachable to the sampling tip.

2. The pressurized appliance as claimed in claim 1, wherein the sampler is configured to cooperate with a pump.

3. The pressurized appliance as claimed in claim 2, wherein the pump is a peristaltic pump.

4. The pressurized appliance as claimed in claim 1, wherein the sampling tip comprises a plurality of sealable orifices distributed radially over the part of the sampling tip extending into the tank.

5. The pressurized appliance as claimed in claim 1, wherein the sampling tip comprises an intermediate part that is removable relative to the cover.

6. The pressurized appliance as claimed in claim 5, wherein the intermediate part extends into the tank when the cover is in the closed position.

7. The pressurized appliance as claimed in claim 6, wherein the intermediate part is configured to screw into the cover.

8. The pressurized appliance as claimed in claim 1, further comprising a cap, wherein:
   the sampling tip comprises a sampling channel that extends along a longitudinal axis of the cannula, and
   when the pressurized appliance is in the first mode, the cap is positioned and held on an end of the sampling tip outside of the tank so as to seal an end of the sampling channel, and the sealable orifice is a through-orifice between the tank and the sampling channel.

9. The pressurized appliance as claimed in claim 1, wherein the cannula comprises a beveled end.

10. The pressurized appliance as claimed in claim 1, wherein the cannula is made of two connectable parts, at least one of the parts being flexible.

11. The pressurized appliance as claimed in claim 1, wherein the tank has a curved bottom.

12. The pressurized appliance as claimed in claim 1, wherein the tank is configured to receive a bucket, which is configured to contain the liquid contents, the cannula extending into the bucket when the cover is in the closed position.

13. The pressurized appliance as claimed in claim 1, wherein the sampler comprises an orifice that cooperates with the sealable orifice in the sampling tip when the pressurized appliance is in the first mode, and that is offset with respect to the sealable orifice in the sampling tip when the pressurized appliance is in the second mode so as to seal the sealable orifice.

14. The pressurized appliance as claimed in claim 13, further comprising a cap, wherein when the pressurized appliance is in the first mode, the cap is positioned and held on an end of the sampler so as to seal the end of the sampler.

15. A method of preparing a culture medium with a pressurized appliance, wherein the pressurized appliance comprises:
   a tank configured to receive liquid contents;
   a cover configured to seal the tank in a closed position;
   a sampling tip removably attached to the cover, the sampling tip comprising:

a cannula configured to contact the liquid contents when the cover is in the closed position, and at least one sealable orifice configured to ensure a pressure equilibrium between the inside of the cannula and the inside of the tank when the cover is in the closed position and the pressurized appliance is in a first mode, and configured to allow sampling of the contents via the cannula when the cover is in the closed position and the pressurized appliance is in a second mode; and a sampler removably attachable to the sampling tip, the method comprising preparing the culture medium with the pressurized appliance when the cover is in the closed position and the pressurized appliance is in the first mode.

* * * * *